United States Patent [19]
Carson et al.

[11] Patent Number: 6,162,810
[45] Date of Patent: Dec. 19, 2000

[54] INADONE AND TETRALONE COMPOUNDS FOR INHIBITING CELL PROLIFERATION

[75] Inventors: Dennis A. Carson, Del Mar; Hsien C. Shih, San Diego; Howard B. Cottam, Fallbrook; Lorenzo Leoni, San Diego, all of Calif.

[73] Assignee: The Regents of the University of California, Oakland, Calif.

[21] Appl. No.: 09/148,576

[22] Filed: Sep. 4, 1998

Related U.S. Application Data

[60] Provisional application No. 60/066,060, Nov. 17, 1997.

[51] Int. Cl.$^7$ .......................... A61K 31/36; A61K 31/44; C07D 211/00; C07D 213/02
[52] U.S. Cl. .......................... 514/277; 514/465; 514/506; 514/532; 514/569; 546/348; 546/339; 546/346; 549/440; 549/366; 560/21; 560/100; 562/488; 562/490
[58] Field of Search ..................................... 514/277, 465, 514/506, 532, 569; 549/440, 366; 546/348, 339, 346; 560/21, 100; 562/488, 490

[56] References Cited

U.S. PATENT DOCUMENTS 3,843,665 10/1974 Coombs et al. .
4,162,162 7/1979 Dueber .

OTHER PUBLICATIONS

Bahner, Carl, et al., "Benzylideneindenes with Oxygen Attached to the Indene Ring," *J. Med. Chem.* (1969) vol. 12, No. 4, 721–2.

Henin, Jacques, et al., Hexahydro–5, 6, 6a, 7, 12, 14 isoquino[2,3–b] benzazepine–2. Novel Access. *J. Heterocycl. Chem.* (1986) vol. 23, No. 4, 975–9.

Gupta, Rajive, et al., "Improved Microwave–induced Synthesis of Chalcones and Related Enones." *Indian J. Chem.*, Sect. B, Org. Chem. Incl. Med. Chem. (1995) vol. 34B(1), 61–2. (Abstract).

Ghannoum et al., Microbios. (1989), 60(242), 23–33.

Levai et al., Pharmazie. (1992), 47(1), 56–7.

Bloxham et al., J. Chem. Soc. Perkin Trans. (1993), 24, 3055–9.

Sergejew et al., J. Enzyme Inhibition, (1994), 8 113–122.

Fies et al., J. Prakt. Chem., (1995), 337, 596–8.

Lankin et al. J. Heterocycl. Chem., (1973) 10(6), 1035–8.

Henin et al. J. Heterocycl. Chem., (1986) 23, 975–9.

Kuck et al. Chem. Ber., (1987) 120, 589–95.

Vavache–Beranger et al. Farmaco–Ed. Sc., (1987) 42(6), 465–73.

*Primary Examiner*—Joseph K. McKane
*Assistant Examiner*—Taofiq A. Solola
*Attorney, Agent, or Firm*—Townsend and Townsend and Crew, LLP

[57] ABSTRACT

A new family of inadone and tetralone tubulin-binding compounds (TBs) is disclosed. Unlike classical TBs, which inhibit mitosis among affected dividing cells, the TBs of the invention possess two unique properties: (1) they induce apoptosis among stationary phase (non-dividing) malignant cells, yet do not impair the viability of normal nonproliferating cells; and, (2) they affect cells which have acquired MDR more powerfully than they affect cells without MDR. Thus, the TBs of the invention provide means to target malignant cells for chemotherapy, even after previous therapies have failed, without affecting normal cells and tissues in the host.

42 Claims, 5 Drawing Sheets

INADONE AND TETRALONE COMPOUNDS FOR INHIBITING CELL PROLIFERATION

This Appln. claims the benefit of Prov. Appl. No. 60/066,060 filed Nov. 17, 1997.

STATEMENT AS TO FEDERALLY SPONSORED RESEARCH

This invention was made with Government support under Grant No. GM23200 and Grant No. AR07567, awarded by the National Institutes of Health. The Government has certain rights in this invention.

BACKGROUND FOR THE INVENTION

1. Field of the Invention

The invention relates to pharmaceutical agents which are cytotoxic in tumor cells. In addition, the invention relates to pharmaceutical agents for use in treating cells which have acquired resistance to chemotherapeutic agents; i.e., cells with multiple drug resistance.

2. History of the Related Art

One of the greatest limitations on the efficacy of cancer chemotherapy is the tendency of cancer cells to develop broad-spectrum resistance to a host of anti-cancer and cytotoxic drugs. Such multiple drug resistance (MDR) is believed to occur to varying degrees in most cancers, either from the onset of the cancer or on recurrence following chemotherapy.

MDR is believed to be mediated by the activity of a cell surface phospho-glycoprotein, P-glycoprotein. Increased expression of the gene which encodes P-glycoprotein (mdr) is found in many malignant cells and may be upregulated by the onset of a malignancy and/or cellular contact with chemotherapeutic agetns. Once active, P-glycoprotein is believed to function as a "hydrophobic vacuum cleaner" which expels hydrophobic drugs from targeted cells. Such drugs include a host of anti-cancer drugs and cytotoxic agents, such as the Vinca alkaloids (e.g., vinblastine), the anthracyclines (e.g., doxorubicin), the epipodophyllotoxins (e.g., etoposide), the taxanes (e.g., taxol), antibiotics (e.g., actinomycin D), antimicrotubule drugs (e.g., colchicine), protein synthesis inhibitors (e.g., puromycin), toxic peptides (e.g., valinomycin), topoisomerase inhibitors (e.g., topotecan), DNA intercalators (e.g., ethidium bromide) and anti-mitotics.

MDR has been the subject of intense research for many years. Efforts to counter MDR have involved the use of hydrophobic competitors for P-glycoprotein binding (such as calcium channel blockers, cephalosporins, steriods, immunosuppressants, antihypertensives, anti-arrhythmics, lipophilic cations, detergents and antidepressants) and tubulin-binding compounds, which inhibit polymerization of membrane-bound microtubulin at sites other than those targeted by antimicrotubule drugs. To varying degrees, most of these competitors eventually fail to sufficiently overcome MDR for reasons including their interference with chemotherapeutic drug uptake, unexpected toxicities and, in the case of the tubulin-binders, tubulin isotype switching.

SUMMARY OF THE INVENTION

The invention provides a new family of tubulin-binding compounds (TBs). Unlike classical TBs, which inhibit mitosis among affected dividing cells, the TBs of the invention possess two unique properties: (1) they induce apoptosis among stationary phase (non-dividing) malignant cells, yet do not impair the viability of normal nonproliferating cells; and, (2) they affect cells which have acquired MDR more powerfully than they affect cells without MDR. Thus, the TBs of the invention provide means to target malignant cells for chemotherapy, even after previous therapies have failed, without affecting normal cells and tissues in the host.

One aspect of the invention is a TB compound of formula 1:

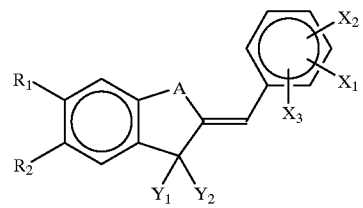

where A is $(CH_2)n$, and n is 1 or 2; $R_1$ and $R_2$ are each independently H, lower alkyl, lower alkoxy, halo, NO, $NO_2$, $NH_2$, acyl, acyloxy, acylamino, diacyl, carboxyacyl, aminooxalyl, or together form —O—$(CH_2)_a$—O—, where a is 1, 2, or 3; $Y_1$ and $Y_2$ are each independently H, OH, or together form =O or =NOH; and $X_1$, $X_2$, and $X_3$ are each independently H, halo, OH, lower alkyl, lower alkoxy, $NO_2$, $NH_2$, acyl, acyloxy, aryl, heteroaryl, acylphosphonate, or together form —O—$(CH_2)_b$—O—, where b is 1, 2, or 3.

Another aspect of the invention is a TB compound of formula 2:

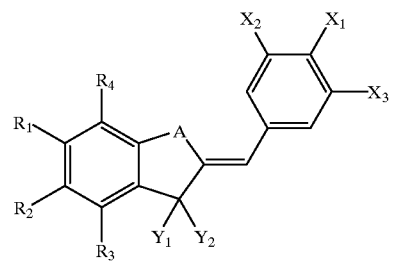

where A is $(CH_2)n$, and n is 1 or 2; $R_1$ and $R_2$ are each independently H, lower alkyl, lower alkoxy, halo, NO, $NO_2$, $NH_2$, acyl, acyloxy, acylamino, diacyl, carboxyacyl, aminooxalyl, or together form —O—$(CH_2)_a$—O—, where a is 1, 2, or 3; $R_3$ is H, $NO_2$, $NH_2$, acyloxy, carboxyacyl, or O—C—O—Z, where Z is O-aryl or —CO-carboxyacyl; $R_4$ is H, acyl, acyloxy or carboxyacyl; Y1 and $Y_2$ are each independently H, OH, or together form =O or =NOH; and $X_1$, $X_2$, and $X_3$ are each independently H, halo, OH, lower alkyl, lower alkoxy, $NO_2$, $NH_2$, acyl, acyloxy, aryl, heteroaryl, acylphosphonate, or together form —O—$(CH_2)_b$—O—, where b is 1, 2, or 3.

Another aspect of the invention is a TB compound of formula 3:

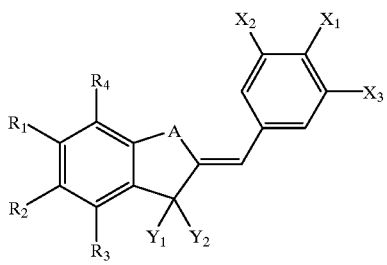

where A is $CH_2$; $R_1$ and $R_2$ are each methyl or methyloxy; $Y_1$ and $Y_2$ together form =O or =NOH; $X_1$ and $X_3$ are methyl or methyloxy; and $X_2$ is H or OH.

Another aspect of the invention is a TB compound of formula 4:

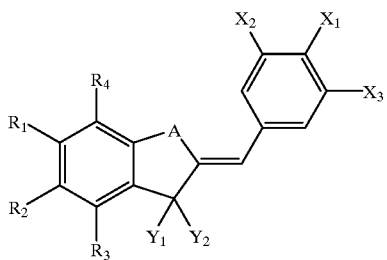

where A is $CH_2$; $R_1$ and $R_2$ are each methyl or methyloxy; $R_3$ is $NO_2$, $NH_2$, acyloxy, carboxyacyl; $Y_1$ and $Y_2$ together form =O or =NOH; $X_1$ and $X_3$ are methyl or methyloxy; and $X_2$ is H or OH.

Another aspect of the invention is a method for inducing apoptosis in tumor cells comprising treating the cells with a pharmaceutical composition including a TB compound of the invention and a pharmaceutical carrier.

Another aspect of the invention is a method for inducing apoptosis in MDR tumor cells comprising treating the cells with a pharmaceutical composition including a TB compound of the invention and a pharmaceutical carrier.

Another aspect of the invention is a method for inducing apoptosis in stationary phase tumor cells comprising treating the cells with a pharmaceutical composition including a TB compound of the invention and a pharmaceutical carrier.

Another aspect of the invention is a method for inducing apoptosis in virus infected cells with MDR comprising treating the cells with a pharmaceutical composition including a TB compound of the invention and a pharmaceutical carrier.

Any of the methods of the invention directed at tumor cells may be practiced as single agent therapy, or as combination therapy in conjunction with the application of other anti-cancer agents. Any of the methods of the invention directed at virus infected cells may be practiced as single agent therapy, or as combination therapy in conjunction with the application of other anti-viral agents.

BRIEF DESCRIPTION OF THE DRAWINGS

FIG. 3(a) shows the effects of TB compound treatment of control cells. FIG. 3(b) shows that 85% of MCF-7/ADR cells enter the $G_1$ phase when the cells are allowed to remain confluent for 1 week. FIG. 3(c) shows the cytotoxic effects of TB compounds on MCF-7/ADR cells.

FIG. 4(a) represents untreated, control cells. FIGS. 4(b) through 4(h) represent cells treated with TB compound no. IK-178 at intervals up to 24 hours. At each time point, cells were harvested, stained and analyzed by flow cytometry. The % numbers in each figure represent the percentage of total cells in the $G_2$/M (mitosis) stage. Darkly shaded areas represent cells in the $G_0$/$G_1$ phase of growth, cross-hatched areas represent cells in the S phase of growth and white areas represent apoptotic cells.

DETAILED DESCRIPTION OF THE INVENTION

Figure 1:
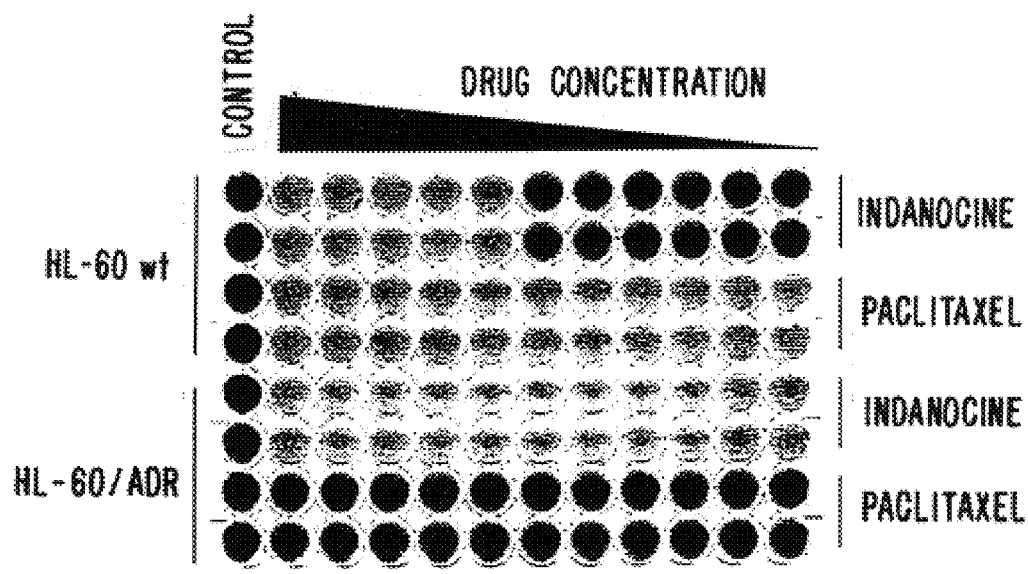
FIG. 1 displays results evidencing the acquisition of collateral sensitivity to the TB compounds of the invention by malignant MDR cells, as compared to wild-type (wt) cells (here, HL-60 (wt) and HL-60/ADR (MDR) cells) and as compared to the effect of the TB drug paclitaxel on the same cells. The first column shown in the drawing represents a control (untreated cells). Dosages increase in each well (at serial dilutions of 1:2) from 1 $\mu$M TB compound (no. IK-178; formula 4) and 10 $\mu$M paclitaxel, respectively, in the second column to 1 nM IK-178 and 10 nM paclitaxel, respectively, in the last columns. Dark wells have growing cells; white wells have apoptotic cells.

A. Definitions of Chemical Terms:

Definitions of standard chemical terms used in this disclosure are provided below. Those of ordinary skill in the art will be familiar with, or can readily interpret, all such chemical names without reference to the definitions provided. Thus, the definitions are provided solely to enable those of lesser skill in the chemical arts to understand the disclosure and are not intended to limit the scope of the invention, which is defined by the appended claims.

1. The term "alkyl" refers to a saturated hydrocarbon radical, which may be straight or branched, having from 1 to 20 carbon atoms. Exemplary alkyl groups include, without limitation, methyl, butyl, I-butyl, dodecyl, hexyl; and the like. The term "lower alkyl" refers to an alkyl radical having from 1 to 6 carbon atoms. Exemplary lower alkyl radicals include methyl, ethyl, propyl, 2-propyl, butyl, 2-butyl, pentyl, hexyl, and the like. The term "cycloalkyl" refers to an alkyl radical having a saturated ring, such as cyclohexyl, cyclopentyl, and the like, and includes cycloalkyl-alkyl radicals such as cyclopentylmethyl, cyclohexylethyl, and the like.

2. The term "aryl" refers to an unsaturated hydrocarbon radical of 5 to 20 carbon atoms, having one or more rings, at least one of which is aromatic. Exemplary aryl radicals include, without limitation, phenyl, naphthyl, indanyl, and the like. Aryl groups may also be substituted with 1 to 3 substituents selected from the group consisting of lower alkyl, alkoxy, acyl, acyloxy, nitro, amino, hydroxy, halo, and dioxy-methylene bridges of the form —O($CH_2$)$_x$O—, where x is 1, 2, or 3. The term "aralkyl" refers to an aryl group linked to the remainder of the molecule by a lower alkyl radical, such as benzyl. The term "heteroaryl" refers to an aryl or aralkyl group having one or more heteroatoms selected from the group consisting of O, N, S, and P. Exemplary heteroaryl radicals include, without limitation, pyridyl, pyrid-4-ylmethyl, furyl, and imidazolyl.

3. The term "alkoxy" refers to a radical of the formula RO—, where R is lower alkyl or cycloalkyl as defined above. Suitable alkoxy radicals include methoxy, ethoxy, prop-2-yloxy, cyclohexyloxy, and the like.

4. The term "acyl" refers to a radical of the formula RC(O)—, where R is lower alkyl, aryl, or cycloalkyl as defined above. Suitable acyl radicals include formyl, acetyl, propionyl, and the like. The term "acyloxy" refers to radicals of the formula RC(O)O—, where R is lower alkyl or cycloalkyl as defined above. Suitable acyloxy radicals include $CH_3COO$, $CH_3CH_2COO$—, benzoyloxy, and the like.

B. Structure and Synthesis of TB Compounds of the Invention:

One aspect of the invention is a TB compound of formula 1:

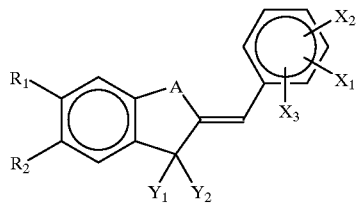

where A is ($CH_2$)n, and n is 1 or 2; $R_1$ and $R_2$ are each independently H, lower alkyl, lower alkoxy, halo, NO, $NO_2$, $NH_2$, acyl, acyloxy, acylamino, diacyl, carboxyacyl, aminooxalyl, or together form —O—($CH_2$)$_a$—O—, where a is 1, 2, or 3; $Y_1$ and $Y_2$ are each independently H, OH, or together form =O or =NOH; and $X_1$, $X_2$, and $X_3$ are each independently H, halo, OH, lower alkyl, lower alkoxy, $NO_2$, $NH_2$, acyl, acyloxy, aryl, heteroaryl, acylphosphonate, or together form —O—($CH_2$)$_b$—O—, where b is 1, 2, or 3.

Another aspect of the invention is a TB compound of formula 2:

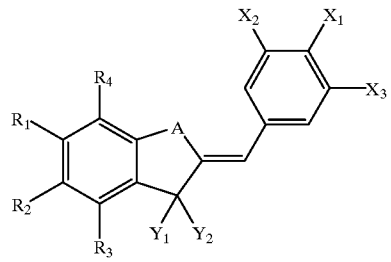

where A is ($CH_2$)n, and n is 1 or 2; $R_1$ and $R_2$ are each independently H, lower alkyl, lower alkoxy, halo, NO, $NO_2$, $NH_2$, acyl, acyloxy, acylamino, diacyl, carboxyacyl, aminooxalyl, or together form —O—($CH_2$)$_a$—O—, where a is 1, 2, or 3; $R_3$ is H, $NO_2$, $NH_2$, acyloxy, carboxyacyl, or O—C—O—Z, where Z is O-aryl or —CO-carboxyacyl; $R_4$ is H, acyl, acyloxy or carboxyacyl; Y1 and $Y_2$ are each independently H, OH, or together form =O or =NOH; and $X_1$, $X_2$, and $X_3$ are each independently H, halo, OH, lower alkyl, lower alkoxy, $NO_2$, $NH_2$, acyl, acyloxy, aryl, heteroaryl, acylphosphonate, or together form —O—($CH_2$)$_b$—O—, where b is 1, 2, or 3.

Another aspect of the invention is a TB compound of formula 3:

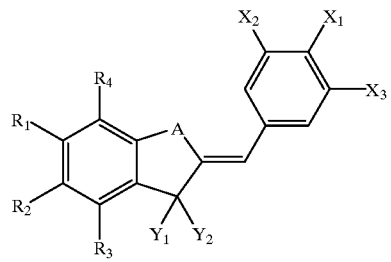

where A is $CH_2$; $R_1$ and $R_2$ are each methyl or methyloxy; Y1 and $Y_2$ together form =O or =NOH; $X_1$ and $X_3$ are methyl or methyloxy; and $X_2$ is H or OH.

Another aspect of the invention is a TB compound of formula 4:

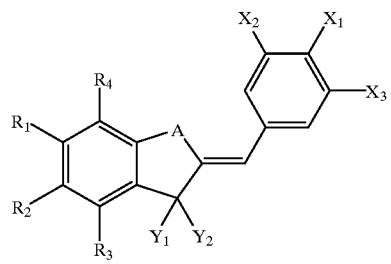

where A is $CH_2$; $R_1$ and $R_2$ are each methyl or methyloxy; $R_3$ is $NO_2$, $NH_2$, acyloxy, carboxyacyl; Y1 and $Y_2$ together form =O or =NOH; $X_1$ and $X_3$ are methyl or methyloxy; and $X_2$ is H or OH.

All of the compounds of the invention may be prepared by standard synthetic methods; for example, those described in Example I. In general, a compound of the invention wherein n=2 and $Y_1$ and $Y_2$ together form =O (i.e., a tetralone derivative) may be prepared by aldol condensation of the appropriately-substituted tetralone with a substituted benzaldehyde derivative under basic (e.g., 1N NaOH/EtOH) or acidic (40% $H_2SO_4$) conditions. Compounds wherein $Y_1$ is HO— and $Y_2$ is H may be prepared from this product by reduction with a suitable reducing agent, such as diisopropyl aluminum hydride. Compounds wherein $Y_1$ and $Y_2$ together form =NOH may be formed from the carbonyl product by treatment with hydroxylamine. Compounds of the invention wherein n=1 (i.e., an indanone derivative) are prepared in the same manner, substituting 1-indanone for 1-tetralone.

C. Activity of TB Compounds of the Invention

1. Presumed mechanism of action.

Although the invention is not limited by any theory as to the mechanism of action of the claimed TB compounds, observations concerning the effects of the compounds on stationary phase and slow-growing MDR cells underscore the unique properties offered by the compounds. As demonstrated by the following discussion and the data set forth in this disclosure, the TB compounds of the invention are active in vitro (Examples III through VI) and in vivo (Example II), making them suitable candidates for clinical applications.

Figure 3:
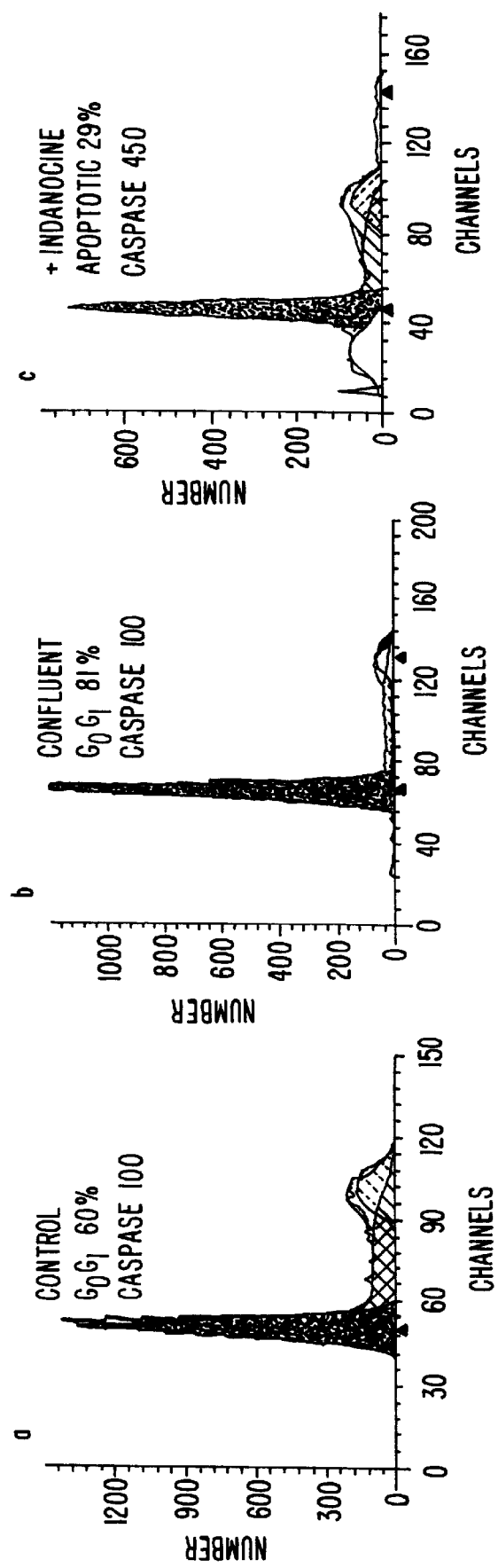
FIG. 3 shows the results of FACS analysis to determine the influence of the TB compounds of the invention on growth cycling of cells.
Figure 4:
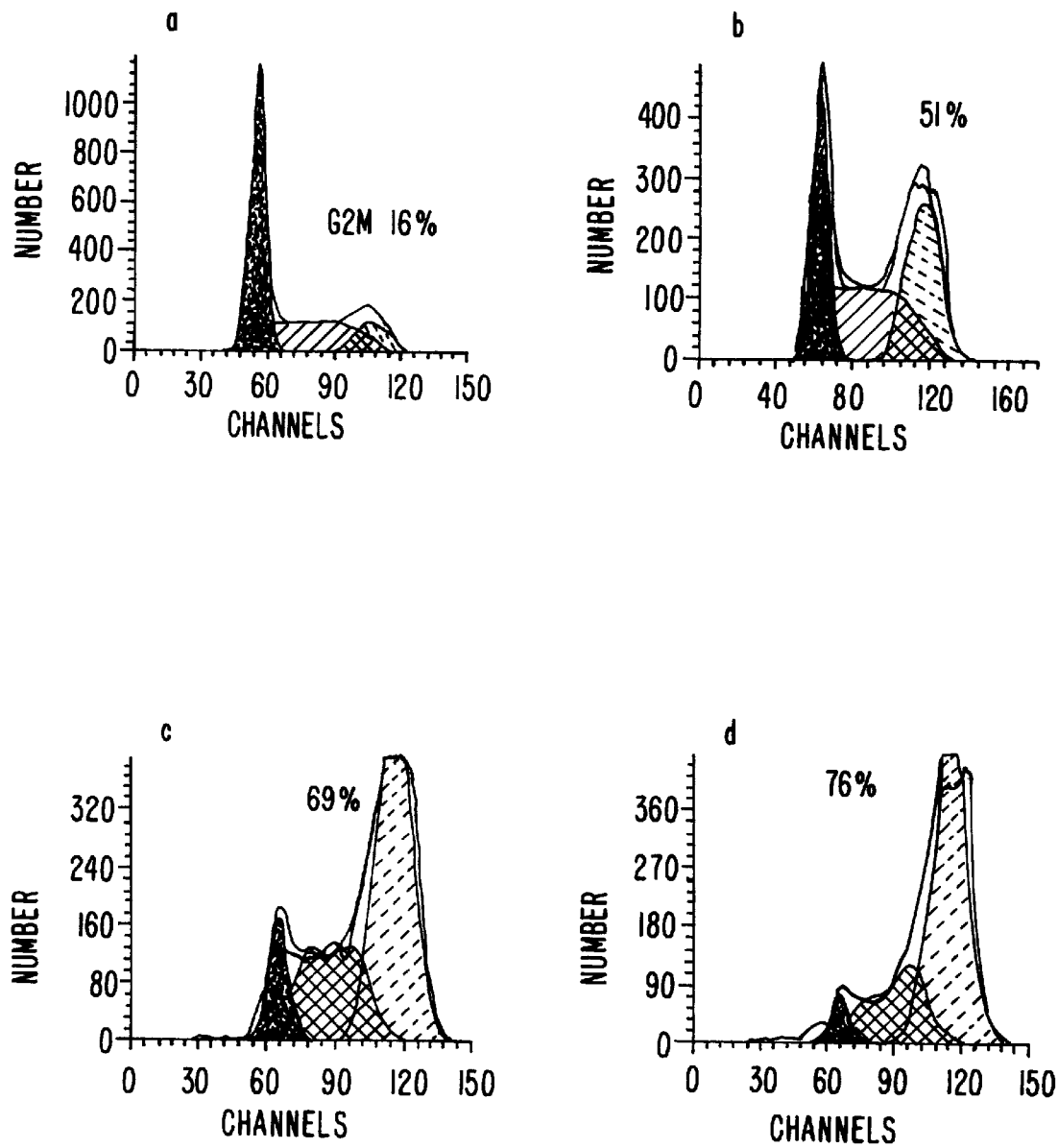
FIG. 4 depicts the stages at which growth of malignant human Jurkat cells with and without MDR is arrested.

As described in Example VII, screening of malignant cells lines treated with TB compounds of the invention demonstrated that the compounds bind tubulin at the colchicine-binding site (FIG. 6) and affect tubulin activity at concentrations equivalent to those utilized for tubulin-binding drugs podophyllotoxin and combretastatin A-4 (see, e.g., Chen, et al., J.Med.Chem., 40:3049–3056 (1997)). Surprisingly, unlike other tubulin-binding agents (which typically do not affect the $G_0$–$G_1$ growth cycle), TB compounds of the invention arrest the growth of MDR cells in $G_1$ phase at nanomolar concentrations (Example VI; FIGS. 3 and 4). Thus, the compounds of the invention kill stationary phase and slow-growing cells which are resistant to the effects of other tubulin-binding agents.

The compounds of the invention are active in a variety of MDR cell types, including those whose resistance is primarily owing to overexpression of p-glycoprotein and of mdr (Example V). Such cells acquire collateral sensitivity to the compounds of the invention by virtue of preceding treatment with other pharmaceutical agents and acquisition of MDR. Surprisingly, MDR cells are more sensitive to the compounds of the invention than are cells without MDR (see, comparative data set forth in: Examples IV and VI; FIGS. 1–5).

Because of the broad scope of activity possessed by the TB compounds of the invention, it is probable that their uptake and cytotoxicity neither depends, nor directly influences, the p-glycoprotein multidrug transporter. As such, this may help to explain how the compounds of the invention are retained in, rather than expelled from, targeted cells.

Whatever the precise intracellular target of the TB compounds of the invention, it is apparently one which is associated with malignancy and/or MDR acquisition and therefore either not present, or not accessible, in normal proliferating cells contacted by the compounds, whose growth and integrity are not affected by the compounds. Thus, the inventive compounds allow targeting of the large factor of non-cycling cells present in many solid tumors, as well as cancers in stationary phase cells (e.g., those in remission), while not posing any risk to the majority of normal tissues. Because the performance of the inventive compounds actually improves in MDR cells, the compounds provide a means to continue or supplement chemotherapy of malignancies and infections while avoiding the obstacles presented by acquisition of MDR in targeted cells.

To these ends, the compounds of the invention are administered to a host for the purpose of inhibiting growth and inducing apoptosis in targeted cells; e.g., malignant and other hyperproliferative cells, infected cells and cells being treated for either condition which have acquired MDR. The compounds of the invention may be administered alone for use in single agent therapy, together with another pharmaceutical agent for use in combination therapy, or following a course of treatment for use in MDR cells. In general, it is anticipated that the inventive TB compounds will be active and therapeutic at dosage levels equivalent to those utilized for existing tubulin-binding drugs, although the collateral sensitivity acquired by MDR cells should enable lower dosages to be applied in therapies directed to those cells. Also, in general, increasing dosage shifts the activity of the inventive TB compounds toward induction of apoptosis (Example IV). Using these data and knowledge of clinically acceptable dosage levels for known TB compounds (bearing in mind the greater activity of the present TB compounds in MDR cells), the identification and application of clinically acceptable dosage ranges for the compounds of the invention within these parameters is well within the ordinary level of skill in the art.

Compounds of the invention may be tested for activity using any generally accepted test for cell proliferation and/or viability. It is currently believed that compounds of the invention activate the JNK kinase system: thus, one may assay compounds of the invention using a commercial assay for JNK activity, such as that provided by New England Biolabs (Beverly, Mass.). Alternatively, one may employ assays as described in the Examples below. In general, compounds may be tested by providing a sample of cells believed to be susceptible (along with suitable positive and negative control cell lines), contacting the cells with the test compound in a range of dilutions, and determining an effective dose. The effective dose may be, for example, the concentration of compound required to kill 50% of the test cells, which may be measured by standard techniques such as $^{51}Cr$ labeling. Alternatively, one may measure the inhibition of proliferation, for example by measuring the reduction in $^3H$-Thy uptake. Compounds of the invention may also be tested in suitable in vivo models, for example by treating nude mice implanted with susceptible tumor cells, and recording the survival rates of treated and control animals.

In employing a compound of the invention for treatment of cancer or other hyperproliferative disease, any pharmaceutically acceptable mode of administration can be used. A compound of the invention can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. A compound of the invention can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and a compound of the invention. In addition, these compositions may include other active agents, carriers, adjuvants, etc.

Generally, depending on the intended mode of administration, the pharmaceutically acceptable composition will contain about 0.1% to 90%, preferably about 0.5% to 50%, by weight of a compound of the invention, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975.

Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of a compound of the invention contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the a compound of the invention in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as a compound of the invention are known in the art. See, U.S. Pat. No. 3,845,770 (describing elementary osmotic pumps); U.S. Pat. No. 3,995,651, U.S. Pat. No. 4,034,756 and U.S. Pat. No. 4,111,202 (describing miniature osmotic pumps); U.S. Pat. No. 4,320,759 and U.S. Pat. No. 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Formulations of a compound of the invention may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns (see, e.g., U.S. Pat. No. 5,364,838, which discloses a method of administration for insulin that can be adapted for the administration of a compound of the invention in the present invention).

EXAMPLES

The following examples are put forth so as to provide those of ordinary skill in the art with a complete disclosure and description of how to carry out the methodology and make and use the invention, and are not intended to limit the scope the invention claimed. Efforts have been made to ensure accuracy with respect to numbers used (e.g., temperature, activity, etc.) but some experimental errors and deviations should be expected. Unless indicated otherwise, temperature is in degrees centigrade, pressure is at or near atmospheric, and oxygen and air content are normal.

Example I

Preparation of Compounds of the Invention (A) General Preparation (Base): A mixture of 6,7-dimethoxy-1-tetralone (200 mg, 0.97 mmol) (n=2) or 5,6-dimethoxyindanone (200 mg 1.04 mmol) (n=1) and an aryl aldehyde (1 equivalent) are stirred in 20 ml 1N NaOH in EtOH at 50° C. overnight. The mixture is diluted with methanol and filtered. The residue is washed several times with MeOH, followed by water to afford almost pure product. If necessary, the product may be purified by chromatography with 2–5% acetone/$CH_2Cl_2$.

(B) First Alternate Preparation (Acid): A mixture of 6,7-dimethoxy-1-tetralone (200 mg, 0.97 mmol) (n=2) or 5,6-dimethoxyindanone (200 mg 1.04 mmol) (n=1) and an aryl aldehyde (1 equivalent) are stirred in 20 ml 40% $H_2SO_4$ at 90° C. for 5 hours. The reaction mixture is filtered, and washed several times with MeOH to afford nearly pure product. If necessary, the product may be purified by chromatography with 2–5% acetone/$CH_2Cl_2$.

(C) Second Alternate Preparation (Acid): A mixture of 6,7-dimethoxy-1-tetralone (200 mg, 0.97 mmol) (n=2) or 5,6-dimethoxyindanone (200 mg 1.04 mmol) (n=1) and an aryl aldehyde (1 equivalent) is stirred in 20 ml $CF_3COOH$ at reflux for 5 hours. The reaction mixture is filtered, and washed several times with MeOH to afford nearly pure product. If necessary, the product may be purified by chromatography with 2–5% acetone/$CH_2Cl_2$.

(D) Third Alternate Preparation (Acid): A mixture of 6,7-dimethoxy-1-tetralone (200 mg, 0.97 mmol) (n=2) or 5,6-dimethoxyindanone (200 mg 1.04 mmol) (n=1) and an aryl aldehyde (1 equivalent) is stirred in 20 ml 5% $CF_3SO_3H$ in glacial acetic acid at 100° C. for 4 hours. The reaction mixture is evaporated, and the residue washed several times with MeOH to afford nearly pure product. If necessary, the product may be purified by chromatography with 2–5% acetone/$CH_2Cl_2$.

(E) Fourth Alternate Preparation (Base): A mixture of 6,7-dimethoxy-1-tetralone (200 mg, 0.97 mmol) (n=2) or 5,6-dimethoxyindanone (200 mg 1.04 mmol) (n=1) and an aryl aldehyde (1 equivalent) are stirred in 20 ml piperidine at 130° C. overnight. The reaction mixture is evaporated, and the residue washed several times with MeOH, followed by water to afford almost pure product. If necessary, the product may be purified by chromatography with 2–5% acetone/$CH_2Cl_2$.

(F) Oxime Preparation: Compounds prepared by the preceding procedures are converted to oximes by stirring with hydroxylamine in pyridine at 100° C. overnight.

(G) Tetradione: A mixture of (E)-6,7-dimethoxy-2-(3',5'-dimethoxyphenylmethylene)-1-tetralone (1 g) and $SeO_2$ (5 eq) in dry 1,4-dioxane (50 ml) was heated at reflux under argon for 8 hr. The reaction mixture was filtered and evaporated. The residue was chromatographed (2% acetone in $CH_2Cl_2$) to provide 240 mg of (E)-6,7-dimethoxy-2-(3',5'-dimethoxybenzylidene)-1,4-tetradione (yield 23%; mp=166–167° C.; ms=407 (MK+); for $C_{21}H_{20}O_6 \cdot 0.4$ $CH_2Cl_2$ calc C=63.88, H=5.21, found C=64.09, H=5.05).

(H) Proceeding as described above, TB compounds of the invention were prepared, including the following compounds whose physical and chemical properties are noted:

6,7-dimethoxy-2-(3',5'-dimethoxyphenylmethylene)-1-tetralone (yield 72% by method (A). Mp=139° C.;

ms=355 (MH+); for $C_{20}H_{20}O_5$, calc C=71.17, H=6.26, found C=70.89, H=6.31);

5,6-dimethoxy-2-(3',5'-dimethoxyphenylmethylene)-1-indanone (yield 75% by method A; mp=195° C.; ms=363 (MNa+); for $C_{20}H_{20}O_5$.0.2 $H_2O$ calc C=69.83, H=5.92, found C=69.95, H=5.99);

5,6-dimethoxy-2-(3',5'-dichlorophenylmethylene)-1-indanone (yield 59% by method B; mp=227° C.; ms=351 ($MH_2$+); for $C_{18}H_{14}O_3Cl_2$ calc C=61.91, H=4.04, found C=61.57, H=4.17);

5,6-dimethoxy-2-(3',5'-dimethylphenylmethylene)-1-indanone (yield 71% by method D; mp=165° C.; ms=331 (MNa+); for $C_{20}H_{20}O_3$ calc C=77.90, H=6.54, found C=77.48, H=6.70);

5,6-dimethoxy-2-(3',5'-dimethoxyphenylmethylene)-1-hydroximinioindane;

5,6-dimethoxy-2-(3',5'-dimethoxyphenylmethylene)-1-hydroxyindane;

6,7-dimethoxy-2-(3'-acetyl-4'-hydroxyphenylmethylene)-1-tetralone;

6,7-dimethoxy-2-(3',4'-dimethoxyphenylmethylene)-1-tetralone (yield 68% by method (A); mp 154–155° C.; ms 354 (MH+); for $C_{21}H_{22}O_5$.⅓$H_2O$ calc C=69.98, H=6.24, found C=70.19, H=5.99);

6,7-dimethoxy-2-(2'-methoxybenzylidine)-1-tetralone (yield 63% by method (A), mp 153–154° C.; ms 3.25.2 (MH+);

6,7-dihydroxy-2-(3',4'-dihydroxyphenylmethylene)-1-tetralone;

6,7-dimethoxy-2-(3',4',5'-trimethoxyphenylmethylene)-1-tetralone (mp=146–147° C.; ms=385 (MH+); for $C_{22}H_{24}O_6$ calc C=68.74, H=6.29, found C=68.57, H=6.30);

6,7-dimethoxy-2-(4'-hydrocarboxy-3'-hydroxyphenylmethylene)-1-tetralone (yield 25% by method (B); mp 249–250° C.; ms 355 (MH+); for $C_{20}H_{18}O_6.CF_3SO_3H$, calc C=50.0, H=3.80);

6,7-dimethoxy-2-(2',3'-dimethoxyphenylmethylene)-1-tetralone (yield 51% by method (A); mp 170–172° C.; ms 355 (MH+); for $C_{21}H_{20}O_5$, calc C=71.17, H=6.26, found C=71.03, H=6.33);

6,7-dimethoxy-2-(2',6'-dimethylphenylmethylene)-1-tetralone;

6,7-dimethoxy-2-(2',6'-dimethyloxyphenylmethylene)-1-tetralone (yield 70% by method (A); mp 156–157° C.; ms 355 (MH+); for $C_{21}H_{22}O_5$.0.2NaOH calc C=69.60, H=6.17, found C=69.35, H=6.00);

6,7-dihydroxy-2-(2',3'-dihydroxyphenylmethylene)-1-tetralone;

6,7-dihydroxy-2-(3',4',5'-trihydroxyphenylmethylene)-1-tetralone;

6,7-dimethoxy-2-(3'-nitrophenylmethylene)-1-tetralone yield 80% by method D; mp 186–187° C.; ms 340 (MH+); for $C_{19}H_{17}NO_5$.0.6$H_2O$, calc C=65.17, H=5.28, N=4.00, found C=65.53, H=4.86, N=3.87;

6,7-dimethoxy-2-(4'-methoxyphenylmethylene)-1-tetralone (yield 30% by method (A). Mp 156–157° C.; ms 325 (MH+); for $C_{20}H_{20}O_4$, calc C=74.06, H=6.21, found C=73.86, H=6.32);

6,7-dimethoxy-2-(4'-methoxyphenylmethylene)-1-tetralone (yield 73.5% by method (A); mp 130–131° C.; ms 356.2 (MH+));

6,7-dimethoxy-2-(2',5'-dimethoxyphenylmethylene)-1-tetralone (yield 70% by method (A). Mp 152–153° C.; for $C_{21}H_{22}O_5$.0.3 NaOH, calc C=68.84, H=6.13, found C=68.67, H=5.95);

6,7-dimethoxy-2-(2',4'-dimethoxy-6'-hydroxyphenylmethylene)-1-tetralone;

6,7-dimethoxy-2-(4'-hydroxyphenylmethylene)-1-tetralone (yield 31% using method (A), mp 197–199° C.; for $C_{19}H_{18}O_4$.2$H_2O$, expected C=72.69, H=5.91; found C=72.52, H=5.74);

6,7-dimethoxy-2-(4'-aminophenylmethylene)-1-tetralone (yield 41% by method (B), reacting 1-tetralone with 4-acetaminobenzaldehyde. Mp 194° C. (decomposed); ms 310 (MH+); for $C_{19}H_{19}NO_3$.0.5$CH_3SO_3H$ expected C=65.53, H=5.92, N=3.92; found C=65.94, H=5.93, N=3.64);

6,7-dimethoxy-2-(4'-(pyridine-N-oxide) phenylmethylene)-1-tetralone;

6,7-dimethoxy-2-(2',5'-dimethylphenylmethylene)-1-tetralone (yield 46% by method (C). Mp 149–150° C., ms 345 (MNa+); for $C_{21}H_{22}O_3$.0.75 $H_2O$, calc C=75.08, H=7.05, found C=74.93, H=6.67);

6,7-dimethoxy-2-(2',4'-dimethylphenylmethylene)-1-tetralone (yield 44% by method (A); mp 175–77° C.; ms 355 (MH+); for $C_{21}H_{22}O_5$ calc C=71.17, H=6.26, found C=70.99, H=6.34);

6,7-dimethoxy-2-(3',5'-dimethylphenylmethylene)-1-tetralone (yield 75% by method D; mp=125–127° C.; ms=345 (MNa+); for $C_{21}H_{22}O_3$ calc C=78.23, H=6.88, found C=77.83, H=6.88);

6,7-dimethoxy-2-(3',5'-dimethoxy-4'-hydroxyphenylmethylene)-1-tetralone (yield 51% by method D; mp=210–212° C.; ms=361 (MNa+); for $C_{21}H_{22}O_4$.0.1 $H_2O$ calc C=74.14, H=6.58, found C=73.92, H=6.34);

6,7-dimethoxy-2-(3'-nitrophenylmethylene)-1-tetralone;

5,6-dimethoxy-2-(3'-chlorophenylmethylene)-1-tetralone (yield 81.5% by method D, mp 150–151° C.; ms 329.2 (MH+); for $C_{19}H_{16}O_3Cl_2$.0.1$H_2O$, calc C=62.57, H=4.47, found C=62.36, H=4.33);

6,7-dimethoxy-2-(3',5'-dichlorophenylmethylene)-1-tetralone (yield 70% by method (B). Mp=200–201° C.; ms=363.1 (MH+); for $C_{19}H_{16}O_3C_{12}$.0.1 $H_2O$, calc C=62.57, H=4.47, found C=62.36, H=4.33);

6,7-dimethoxy-2-(4'-methoxybenzylidene)-1-tetralone (yield 30% by method A; mp=157–157° C.; ms 325 (MH+); for $C_{20}H_{20}O_4$ calc C=74.06, H=6.21, found C=73.86, H=6.32);

5,6-dimethoxy-2-(2'-hydroxy4',6'-diiodophenylmethylene)-1-indanone;

5,6-dimethoxy-2-(2'-hydroxy-3',5'-diiodophenylmethylene)-1-indanone (yield 46% by method B; mp=285° C. (decomposed); ms=549 (MH+); for $C_{18}H_{14}O_4I_2$.0.7 $H_2SO_4$ calc C=35.05, H=2.50, found C=35.08, H=2.62);

5,6-dimethoxy-2-(2',5'-dimethylphenylmethylene)-1-indanone (yield 76% by method D; mp=100–103° C.; ms=639 ($M_2Na$+); for $C_{20}H_{20}O_3$ calc C=77.90, H=6.54, found C=77.43, H=6.76);

5,6-dimethoxy-2-(uracil-5-yl)-1-indanone;

5,6-methylenedioxy-2-(3',5'-dimethoxyphenylmethylene)-1-indanone (yield 29% by method A; mp=259–269° C. (decomposed); ms=325.2 (MH+); for $C_{19}H_{16}O_5$.0.4 $H_2O$ calc C=68.83, H=5.10, found C=68.60, H=4.86);

5,6-dihydroxy-2-(3',5'-dichlorophenylmethylene)-1-indanone (yield 76% from (E)-5,6-dimethoxy-2-(3',5'-dichlorophenylmethylene)-1-indanone after treatment with $BBr_3$ in $CH_2Cl_2$ at 0° C.-rt overnight; mp=195° C. (decomposed); ms=231 (M+);

5,6-dimethoxy-2-(2',6'-dichloro-4'-pyridin-4-yl)phenylmethylene)-1-indanone;

5,6-dimethoxy-2-(3',5'-ditrifluoromethoxyphenylmethylene)-1-indanone (yield 27% by method A, mp=123–125° C., ms=417 (MH+);

5,6-dimethoxy-2-(3',5'-dimethyl-4'-hydroxyphenylmethylene)-1-indanone (yield 88% by method D; mp=136–137° C.; ms=347 (MNa+); for $C_{20}H_{20}O_4$ calc C=74.06, H=6.21, found C=73.70, H=6.40);

5,6-dimethoxy-2-(2'-hydroxy-5'-nitrophenylmethylene)-1-indanone (yield 69% by method B; mp=195° C.; ms=364 (MNa+); for $C_{18}H_{15}NO_6 \cdot 1.1\ H_2O$ calc C=59.86, H=4.80, found C=59.56, H=4.35);

5,6-dimethoxy-2-(3',5'-difluorophenylmethylene)-1-indanone;

5,6-dimethoxy-2-(3',5'-dimethoxy-1'-hydroxycyclohexylmethylene)-1-indanone;

5,6-dimethoxy-7-nitro-2-(3',5'-dimethyl-4'-hydroxyphenylmethylene)-1-indanone (yield 96% by method D; mp=303° C. (decomposed); ms=370 (MH+); for $C_{20}H_{19}NO_6 \cdot 0.75\ H_2O$ calc C=62.73, H=5.40, N=3.66, found C=62.29, H=5.03, N=3.30);

6-methoxy-2-(3',5'-dimethyl-4'-hydroxyphenylmethylene)-1-indanone (yield 33% by method A; mp=195° C.; ms=317 (MNa+); for $C_{19}H_{18}O_3$ calc C=77.53, H=6.16, found C=77.29, H=5.80);

5-methoxy-2-(3',5'-dimethyl-4'-hydroxyphenylmethylene)-1-indanone (mp=225–226° C.; ms=295 (MH+); for $C_{19}H_{18}O_3$ calc C=77.53, H=6.16, found C=77.29, H=5.54);

5,6-dimethoxy-7-amino-2-(3',5'-dimethyl-4'-hydroxyphenylmethylene)-1-indanone (yield 18% by reducing (E)-5,6-dimethoxy-7-nitro-2-(3',5'-dimethyl-4'-hydroxyphenylmethylene)-1-indanone with $NaHSO_3$ (3 eq) in 1N $NaOH/EtOH-H_2O$ at 80° C. for 4 hr; mp=238–240° C.; ms=340 (MH+); for $C_{20}H_{21}NO_4 \cdot 0.2\ MeOH$ calc C=70.24, H=6.35, N=4.05, found C=70.24, H=5.97, N=3.99);

5,6-dimethoxy-2-(3',5'-dimethyl-4'-phosphonoacetylphenylmethylene)-1-indanone (by heating 5,6-dimethoxy-2-(3',5'-dimethyl-4'-hydroxybenzylidene)-1-indanone at reflux with phosphonoacetic chloride in dry pyridine; mp=220–221°);

5,6-dimethoxy-2-(3',5'-dimethyl-4'-O-succinylphenylmethylene)-1-indanone;

5,6-dimethoxy-2-(3',5'-dimethyl-4'-O-acetoxyphenylmethylene)-1-indanone (yield 83% by heating (E)-5,6-dimethoxy-2-(3',5'-dimethyl-4'-hydroxybenzylidene)-1-indanone at reflux in $Ac_2O$ in pyridine; mp=125–126° C.; ms=367 (MH+); for $C_{22}H_{22}O_5 \cdot 0.5\ MeOH$ calc C=70.66, H=6.33, found C=70.90, H=5.96);

5,6-dimethoxy-2-(3'-chlorophenylmethylene)-1-indanone (mp=189–190° C.; ms=315 (MH+); for $C_{18}H_{15}ClO_3 \cdot 0.2\ MeOH$ calc C=68.03, H=4.96, found C=68.03, H=4.87);

6,7-dimethoxy-2-(3'-pyridylmethylene)-1-tetralone (yield 29% by method E; mp=135–137° C.; ms=296 (MH+); for $C_{18}H_{17}NO_3 \cdot 0.25\ CH_3COCH_3$ calc C=72.68, H=6.02, N=4.52, found C=72.51, H=5.76, N=4.62);

5,6-dimethoxy-2-(2',5'-dimethoxy-4'-hydroxyphenylmethylene)-1-indanone (mp=134–135° C.; ms=341 (MH+); for $C_{20}H_{20}O_5 \cdot 1.2\ H_2O$ calc C=66.36, H=6.24, found C=66.21, H=5.86);

5,6-dimethoxy-2-(3',5'-dimethyl-4'-succinobenzylidene)-1-indanone (yield 80% by heating (E)-5,6-dimethoxy-2-(3',5'-dimethyl-4'-hydroxybenzylidene)-1-indanone at reflux in succinic anhydride in pyridine; ms=425.3 (MH+);

5,6-dimethoxy-2-(3',5'-dimethyl-4'-nitrobenzylidene)-1-indanone (yield 13% by method D; mp=242–243 ° C.; for $C_{20}H_{19}NO_5 \cdot 0.1\ H_2O$ calc C=67.64, H=5.42, N=3.94, found C=67.48, H=5.24, N=3.82);

5,6-dimethoxy-2-(3',5'-dimethoxy-4'-hydroxyphenylmethylene)-1-indanone (yield 58% by method D; mp=216–217° C.; ms=357 (MH+); for $C_{20}H_{20}O_6$ calc C=67.41, H=5.34, found C=67.44, H=5.34); and 5,6-dimethoxy-7-oxalylamino-2-(3',5'-dimethyl-4'-hydroxyphenylmethylene)-1-indanone.

Example II

Cytotoxicity of the TB Compounds of the Invention on Human Jurkat T Cell Leukemia Cells (A) The compounds prepared in Example 1 above were tested for biological activity by culturing human Jurkat T cell leukemia cells for three days at an initial density of $10^5$ cells/ml in RPMI 1640+10% FBS (fetal bovine serum). Compounds of the invention were added, and the concentration necessary to kill 50% ($TC_{50}$) of the cells was determined by $OD_{570/650}$. The results are shown in Table 1.

TABLE 1

Toxicity to Jurkat T cells

| Compound | $TC_{50}$ ($\mu$M) |
|---|---|
| 6,7-dimethoxy-2-(3',5'-dimethoxyphenylmethylene)-1-tetralone | 5.0 |
| 5,6-dimethoxy-2-(3',5'-dimethoxyphenylmethylene)-1-hydroximinioindane | 0.80 |
| 5,6-dimethoxy-2-(3',5'-dichlorophenylmethylene)-1-indanone | 0.75 |
| 5,6-dimethoxy-2-(3',5'-dimethoxyphenylmethylene)-1-hydroxyindane | 0.75 |
| 5,6-dimethoxy-2-(3',5'-dimethoxyphenylmethylene)-1-indanone | 0.75 |
| 5,6-dimethoxy-2-(3',5'-dimethylphenylmethylene)-1-indanone | 0.075 |

(B) Similarly, compounds of the invention were tested for their ability to kill CEM WT, CEM AB9228, MOLT-4, Jurkat, NALL-1, WI-L2, K562, and HL-60 cells. The average $TC_{50}$ is shown in Table 2.

TABLE 2

Cytotoxicity to various proliferating cell lines

| Compound | $TC_{50}$ ($\mu$M) |
|---|---|
| 6,7-dimethoxy-2-(3',4'-dimethoxyphenylmethylene)-1-tetralone | >50 |
| 6,7-dimethoxy-2-(3',5'-dimethoxyphenylmethylene)-1-tetralone | 4 |
| 6,7-dimethoxy-2-(3'-hydrocarboxy-4'-hydroxyphenylmethylene)-1-tetralone | >50 |
| 6,7-dimethoxy-2-(2',3'-dimethoxyphenylmethylene)-1-tetralone | >50 |

TABLE 2-continued

Cytotoxicity to various proliferating cell lines

| Compound | TC$_{50}$ ($\mu$M) |
|---|---|
| 6,7-dimethoxy-2-(2',6'-dimethylphenylmethylene)-1-tetralone | >50 |
| 6,7-dihydroxy-2-(3',4',5'-trihydroxyphenylmethylene)-1-tetralone | 43 |
| 6,7-dimethoxy-2-(3',4',5'-trimethoxyphenylmethylene)-1-tetralone | >50 |
| 6,7-dimethoxy-2-(4'-methoxyphenylmethylene)-1-tetralone | >50 |
| 6,7-dimethoxy-2-(2',5'-dimethoxyphenylmethylene)-1-tetralone | 11 |
| 6,7-dimethoxy-2-(2',4'-dimethoxy-6'-hydroxyphenylmethylene)-1-tetralone | 10 |
| 6,7-dimethoxy-2-(4'-hydroxyphenylmethylene)-1-tetralone | 30 |
| 6,7-dimethoxy-2-(4'-aminophenylmethylene)-1-tetralone | >50 |
| 6,7-dimethoxy-2-(4'-(pyridine-N-oxide)phenylmethylene)-1-tetralone | >50 |
| 6,7-dihydroxy-2-(2',3'-dihydroxyphenylmethylene)-1-tetralone | >50 |
| 6,7-dimethoxy-2-(2',5'-dimethylphenylmethylene)-1-tetralone | 5 |
| 6,7-dimethoxy-2-(3',5'-dimethylphenylmethylene)-1-tetralone | 4 |
| 5,6-dimethoxy-2-(2'-hydroxy-4',6'-diiodophenylmethylene)-1-indanone | 18 |
| 5,6-dimethoxy-2-(2',5'-dimethylphenylmethylene)-1-indanone | 162 |
| 5,6-methylenedioxy-2-(3',5'-dimethoxyphenylmethylene)-1-indanone | >50 |
| 5,6-dihydroxy-2-(3',5'-dichlorophenylmethylene)-1-indanone | 30 |
| 5,6-dimethoxy-2-(2',6'-dichloro-4'-(pyridin-4-yl)phenylmethylene)-1-indanone | 40 |
| 5,6-dimethoxy-2-(3',5'-ditrifluoromethoxyphenylmethylene)-1-indanone | >100 |
| 5,6-dimethoxy-2-(3',5'-dimethyl-4'-hydroxyphenylmethylene)-1-indanone | 0.017 |
| 5,6-dimethoxy-2-(2'-hydroxy-5'-nitrophenylmethylene)-1-indanone | 15 |
| 5,6-dimethoxy-2-(3',5'-difluorophenylmethylene)-1-indanone (trans) | 19 |
| 5,6-dimethoxy-2-(3',5'-difluorophenylmethylene)-1-indanone (cis) | 26 |
| 5,6-dimethoxy-2-(3',5'-dimethoxy-1'-hydroxycyclohexylmethylene)-1-indanone | 2 |
| 5,6-dimethoxy-7-nitro-2-(3',5'-dimethyl-4'-hydroxyphenylmethylene)-1-indanone | >50 |
| 6-methoxy-2-(3',5'-dimethyl-4'-hydroxyphenylmethylene)-1-indanone | >50 |
| 7-methoxy-2-(3',5'-dimethyl-4'-hydroxyphenylmethylene)-1-indanone | 51 |
| 5,6-dimethoxy-7-amino-2-(3',5'-dimethyl-4'-hydroxyphenylmethylene)-1-indanone | 0.005 |
| 5,6-dimethoxy-2-(3',5'-dimethyl-4'-phosphonoacetylphenylmethylene)-1-indanone | 0.007 |
| 5,6-dimethoxy-2-(3',5'-dimethyl-4'-O-succinylphenylmethylene)-1-indanone | 1 |
| 5,6-dimethoxy-2-(3',5'-dimethyl-4'-O-acetoxyphenylmethylene)-1-indanone | |
| 5,6-dimethoxy-2-(3'-chlorophenylmethylene)-1-indanone | >50 |
| 5,6-dimethoxy-2-(3',5'-dimethoxy-4'-hydroxyphenylmethylene)-1-indanone | >50 |
| 5,6-dimethoxy-7-oxalylamino-2-(3',5'-dimethyl-4'-hydroxyphenylmethylene)-1-indanone | 0.004 |
| 5,6-dimethoxy-2-(3',5'-dimethylphenylmethylene)-1-indanone | 0.075 |
| 5,6-dimethoxy-2-(3',5'-dimethoxyphenylmethylene)-1-indanone | 0.75 |
| 5,6-dimethoxy-2-(3',5'-dichlorophenylmethylene)-1-indanone | 0.75 |
| 5,6-dimethoxy-2-(3',5'-dimethoxyphenylmethylene)-1-hydroximinioindane | 0.80 |
| 6,7-dimethoxy-2-(2'-methoxyphenylmethylene)-1-tetralone | >50 |
| 6,7-dimethoxy-2-(3'-nitrophenylmethylene)-1-tetralone | 9 |
| 6,7-dimethoxy-2-(3'-chlorophenylmethylene)-1-tetralone | 9 |
| 6,7-dimethoxy-2-(3'-methoxyphenylmethylene)-1-tetralone | 5 |
| 6,7-dimethoxy-2-(4'-hydroxyphenylmethylene)-1-tetralone | 30 |
| 6,7-dimethoxy-2-(4'-methoxyphenylmethylene)-1-tetralone | >50 |
| 6,7-dimethoxy-2-(2',3'-dimethoxyphenylmethylene)-1-tetralone | >50 |
| 6,7-dimethoxy-2-(2',4'-dimethoxyphenylmethylene)-1-tetralone | >50 |
| 6,7-dimethoxy-2-(2',6'-dimethoxyphenylmethylene)-1-tetralone | >50 |
| 6,7-dimethoxy-2-(3',4'-dimethoxyphenylmethylene)-1-tetralone | >50 |
| 6,7-dimethoxy-2-(3',5'-dichlorophenylmethylene)-1-tetralone | 7 |
| 6,7-dimethoxy-2-(3',5'-dimethoxy-4'-hydroxyphenylmethylene)-1-tetralone | 6 |
| 5,6-dimethoxy-2-(3'-chlorophenylmethylene)-1-indanone | 2.5 |
| 5,6-dimethoxy-2-(2'-hydroxy-5'-nitrophenylmethylene)-1-indanone | 14.5 |
| 5,6-dimethoxy-2-(2',5'-dimethylphenylmethylene)-1-indanone | 30.5 |
| 5,6-dimethoxy-2-(3',5'-dimethoxyphenylmethylene)-1-indanone | 2 |
| 5,6-dimethoxy-2-(3',5'-dimethoxy-4'-hydroxyphenylmethylene)-1-indanone | >50 |
| 5,6-dimethyl-2-(3',5'-dimethoxyphenylmethylene)-1-indanone | >50 |
| 5-methoxy-2-(3',5'-dimethoxyphenylmethylene)-1-indanone | >50 |
| 6-dimethoxy-2-(3',5'-dimethoxy-4'-hydroxyphenylmethylene)-1-indanone | >50 |
| 5,6-dimethoxy-2-(3',5'-difluorophenylmethylene)-1-indanone | 19 |
| 5,6-dimethoxy-2-(3',5'-ditrifluoromethylphenylmethylene)-1-indanone | >50 |
| 5,6-dimethoxy-2-(3',5'-dichlorophenylmethylene)-1-indanone | 2 |
| 2-(3',5'-dichlorophenylmethylene)-1-indanone | 30 |
| 5,6-dimethoxy-2-(2'-hydroxy-3',5'-diiodophenylmethylene)-1-indanone | 12.5 |
| 5,6-dimethoxy-2-(3',5'-dimethylphenylmethylene)-1-indanone | 0.081 |
| 5,6-dimethoxy-2-(3',5'-dimethyl-4'hydroxy-phenylmethylene)-1-indanone | 0.0065 |
| 5,6-dimethoxy-2-(3',5'-dimethyl-4'-acetoxyphenylmethylene)-1-indanone | 0.4 |
| 5,6-dimethoxy-2-(3',5'-dimethyl-4'-succinophenylmethylene)-1-indanone | 0.07 |
| 5,6-dimethoxy-2-(3',5'-dimethyl-4'-phosphonoacetoxyphenylmethylene)-1-indanone | 11.5 |
| 5,6-dimethoxy-2-(3',5'-dimethyl-4'-nitrophenylmethylene)-1-indanone | >50 |
| 5,6-dimethoxy-7-nitro-2-(3',5'-dimethyl-4'-hydroxyphenylmethylene)-1-indanone | >50 |
| 5,6-dimethoxy-7-amino-2-(3',5'-dimethyl-4'-hydroxyphenylmethylene)-1-indanone | 0.0008 |
| 5,6-dimethoxy-7-methoxalylamino-2-(3',5'-dimethyl-4'-hydroxyphenylmethylene)-1-indanone | 0.2 |
| 5,6-dimethoxy-7-oxalylamino-2-(3',5'-dimethyl-4'-hydroxyphenylmethylene)-1-indanone | 0.15 |
| 5,6-dimethoxy-7-(NHCOCOH)-2-(3',5'-dimethyl-4'-hydroxyphenylmethylene)-1-indanone | 0.0015 |

(C) Proceeding as described above, further compounds were tested for their ability to kill proliferating cells. The average TC$_{50}$ is shown in Table 3.

Example III

Growth Inhibitory Activity of TB Compounds of the Invention

To screen the compounds of the invention for growth inhibitory activity, a hollow fiber assay test was performed according to the protocol established by the National Cancer Institute's Developmental Therapeutics Program. Three TB compounds of the invention were selected as representative of the genus of compounds defined by the invention: compound nos. IK-178 (formulae 2 and 4), IK-123 (formulae 2 and 3) and 162 (formulae 2 and 3).

The assay showed that the mean 50% growth inhibitory concentration (GI$^{50}$) of the tested compounds was ≦20 nM.

In 29 out of 49 cell lines, including an adriamycin resistant breast cancer line, the $GI^{50}$ was below the lowest concentration tested (10 nM). Because the TB compounds of the invention are hydrophobic, and therefore susceptible to removal from cells by the "hydrophobic vacuum cleaner" of MDR cells, the compounds' activity toward the MDR cells was surprising.

Briefly, according to the National Cancer Institute, the hollow fiber assay is performed as follows:

"The Biological Testing Branch of the Developmental Therapeutics Program has adopted a preliminary in vivo screening tool for assessing the potential anticancer activity of compounds identified by the large scale in vitro cell screen. For these assays, human tumor cells are cultivated in polyvinylidene fluoride (PVDF) hollow fibers, and a sample of each cell line is implanted into each of two physiologic compartments (intraperitoneal and subcutaneous) in mice. Each test mouse receives a total of 6 fibers (3 intraperitoneally and 3 subcutaneously) representing 3 distinct cancer cell lines. Three mice are treated with potential antitumor compounds at each of 2 test doses by the intraperitoneal route using a QD×4 treatment schedule. Vehicle controls consist of 6 mice receiving the compound diluent only. The fiber cultures are collected on the day following the last day of treatment. To assess anticancer effects, viable cell mass is determined for each of the cell lines using a formazan dye (MTT) conversion assay. From this, the % T/C can be calculated using the average optical density of the compound treated samples divided by the average optical density of the vehicle controls. In addition, the net increase in cell mass can be determined for each sample as a sample of fiber cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as % T/C for each of the 2 compound doses against each of the cell lines with separate values calculated for the intraperitoneal and subcutaneous samples.

Compounds are selected for further in vivo testing in standard subcutaneous xenograft models on the basis of several hollow fiber assay criteria. These include: (1) a % T/C of 50 or less in 10 of the 48 possible test combinations (12 cell lines×2 sites×2 compound doses); (2) activity at a distance (intraperitoneal drug/subcutaneous culture) in a minimum of 4 of the 24 possible combinations; and/or (3) a net cell kill of 1 or more cell lines in either implant site. To simplify evaluation, a points system has been adopted which allows rapid viewing of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score≧8 or a net cell kill of one or more cell lines are referred for xenograft testing. These criteria were statistically validated by comparing the activity outcomes of >80 randomly selected compounds in the hollow fiber assay and in the xenograft testing. This comparison indicated that there was a very low probability of missing an active compound if the hollow fiber assay were used as the initial in vivo screening tool. In addition to these criteria, other factors (e.g. unique structure, mechanism of action) may result in referral of a compound for standard xenograft testing without the compound meeting these criteria."

As tested in the above-described assay, selected TB compounds of the invention demonstrated growth inhibitory properties as follows:

TABLE 3

In vivo Growth Inhibitory Activity

| TB COMPOUND # | IP SCORE | SC SCORE | TOTAL SCORE (IP + SC) | CELL KILL |
|---|---|---|---|---|
| IK-178 | 18 | 6 | 24 | N |
| IK-123 | 6 | 2 | 8 | N |
| 162 | 14 | 12 | 26 | Y |

Testing performed against 60 human cancer cell lines, including leukemias, non-small cell lung cancer, colon cancer, ovarian cancer, melanoma, renal cancer, prostate cancer and breast cancer.

Example IV

Collateral Sensitivity of Various MDR Cell Lines to TB Compounds of the Invention To confirm the results described in Example III, the effect of TB compounds no. IK-178 on the growth of MCF-7 and MCF-7/ADR, MES-SA and MES-SA/DX5, MDA-MB-321 and MDA3-1, HL-60 and HL-60/ADR, CEM and CEM/VLB100, KB-3-1 and GB-GRC-1, and MV522 and MV522/Q6 cells were compared (see, legend to Table 4, below, for properties of each cell line). These paired cell lines provide different multidrug resistance mechanisms, including alterations of gp170 (mdr1 gene), gp180 (MRP gene), and the glutathione transferase π isoform.

In all cell lines tested the antiproliferative concentrations of the TB compounds of the invention were equivalent or lower in the multidrug resistant cells compared to the respective wild type cells. Three of the tested cell lines tested (MCF-7, MES-SA, and HL-60) showed collateral sensitivity to the TB compounds tested; i.e. the MDR cell line was significantly more sensitive than cell line without resistance to the growth inhibitory effects of the TB compounds. Results of the assays are shown in Table 4 below and represent the $GI^{50} \pm 1$ SD (n>5 and p<0.001 by Wilcoxon Signed Rank Test).

TABLE 4

Activity in Cancer Cells With and Without MDR

| | TB Compound IK-178 | | Paclitaxel | |
|---|---|---|---|---|
| CELL LINES | WILD TYPE | MDR | WILD TYPE | MDR |
| MCF-7 & MCF-7/ADR | 20 ± 5 | 4 ± 1 | 50 ± 6 | >10000 |
| MES-SA & MES-SA/DX5 | 85 ± 6 | 12 ± 3 | <1 | >1000 |
| MDA-MB-321 & MDA3-1/gp170 | 10 ± 3 | 25 ± 2 | 50 ± 2 | >1000 |
| HL-60 & HL-60/ADR | 40 ± 3 | 2 ± 0.2 | <1 | >1000 |
| CEM & CEM/VLB100 | 12 ± 2 | 20 ± 1 | <1 | 606 ± 20 |
| KB-3-1 & KB-GRC-1 | 7 ± 2 | 7 ± 3 | 7 ± 3 | >1000 |
| MV522 & MV522/Q6 | 13 ± 3 | 8 ± 2 | 15 ± 4 | 358 ± 8 |

MCF7=human breast adenocarcinoma; MCF7/ADR= human breast adenocarcinoma MDR cells, selected against doxorobucin; MDA-MB-321=human breast adenocarcinoma; MDA3-1/gp170+=MDA-SA MDR cells expressing p-glycoprotein; MES-SA=human uterine sarcoma; MES-SA/DX5=MES-SA MDR cells selected against doxorobucin; HL-60=human acute promyelocytic leukemia; HL-60/ADR=MDR HL-60 cells selected against doxorobucin, with MRP/gp180 expression; CEM=human lymphoblastoid cells; CEM/VLB100=MDR CEM cells, selected against vinblastine, expressing p-glycoprotein; KB-3-1=human carcinoma; KB-GRC-1=MDR KB-3-1 transfectoma, expressing p-glycoprotein; MV522=metastatic human lung carcinoma; MV522/Q6=MDR MV522 transfectoma, expressing p-glycoprotein.

Figure 2:
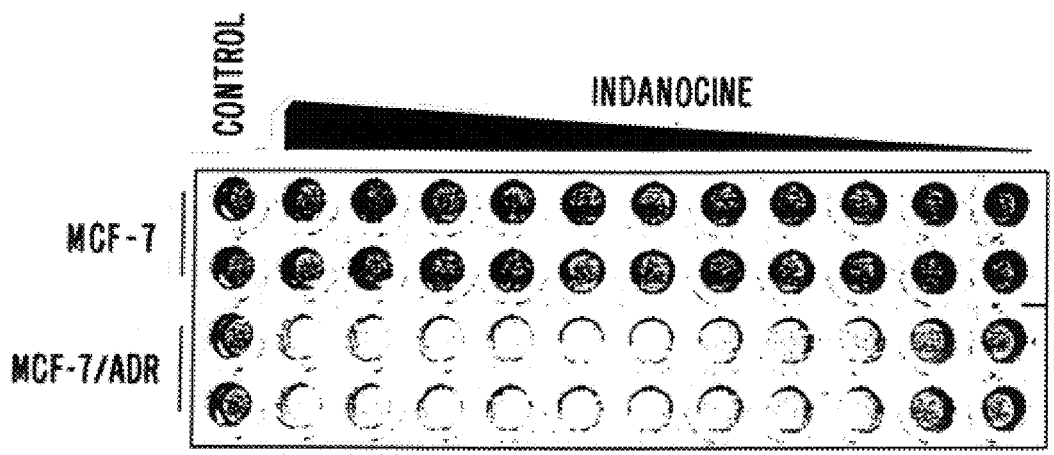
FIG. 2 displays results evidencing the acquisition of collateral sensitivity to the TB compounds of the invention by malignant MDR cells, as compared to wild-type (wt) cells (here, MDF-7 (wt) and MDF-7/ADR (MDR) cells). The first column shown in the drawing represents a control (untreated cells). Dosages increase in each well (at serial dilutions of 1:2) from 1 $\mu$M TB compound (no. IK-178; formula 4) in the second column to 1 nM IK-178 in the last column. Dark wells have growing cells; white wells have apoptotic cells.

A visual example of TB compound induced collateral sensitivity can be seen in a comparison of the effect of the compounds on human HL-60 and MDF-7 cancer cells with and without MDR (FIGS. 1 and 2). Cells from each line were plated in a 96 well plate and then treated for 3 days with decreasing (1:2 dilutions) concentrations of TB compound IK-1 78 (from 1 µM) and the conventional TB drug paclitaxel (from 10 µM). The MTT assay (quantitation of growth by reduction of the yellow dye 3-(4,5-dimethyl-2-thiazolyl)-2,5-dephenyl-2H-tetrazolium bromide (MTT) to a blue formazan product) was then performed at day 3.

Referring to FIGS. 1 and 2, results with HL-60 (upper half) and MDR HL-60/ADR cells (lower half) are shown. The increasing concentrations applied to each well are shown starting at the second column up to the 12$^{th}$ column (the first column is control). The dark wells represent high viability and the clear wells low viability. With acquisition of MDR (in the HL-60/ADR and MDF-7/ADR cells), sensitivity to paclitaxel was lost, but sensitivity to TB compound IK-178 was retained, and even enhanced.

Example V

P-Glycoprotein Expression Does Not Confer Resistance in Cancer Cell Lines to the TB Compounds of the Invention To determine whether increased p-glycoprotein expression would confer resistance to the TB compounds of the invention, the effects of TB compound IK-178 on two carcinoma cell lines (KB-3-1 and MV522) and corresponding transfectoma clones that overexpressed the mdr1 gene (KB-GRC-1 and MV522/Q6) were compared.

To this end, the cells were plated and treated with varying concentrations of TB compound IK-178 or paclitaxel for 72 h. Cell proliferation was assessed by MTT assay. The transfectomas were resistant to paclitaxel, but retained complete sensitivity to TB compound IK-178 (see, Table 4, above).

Example VI

Stationary Phase Cancer Cells are Especially Sensitive to the TB Compounds of the Invention FACS analysis was performed to determine the influence of the TB compounds of the invention on growth cycling of cells (the analysis was performed on harvested cells, fixed in ice-cold 70% ethanol solution, then treated with 100 µg/ml of RNAse A and stained with 50 µg/ml propidium iodide for 1 h at 37° C. DNA content of the cells was analyzed by flow cytometry (Becton Dickinson FACScalibur), and the cell cycle distribution was calculated with the program ModFit LT 2.0 (Verity Software)).

As determined by the analysis, up to 85% of MCF-7/ADR cells enter the $G_1$ phase of the cell cycle when the cultures were allowed to remain confluent for 1 week (FIG. 3(b), middle panel). Remarkably, TB compound treatment of stationary phase MDR cells, but not parental cells, resulted in cell death (IC$_{50}$ 32 nM) (FIG. 3(a)).

The cytotoxic effect of the TB compounds (represented by compound no. IK-178) in noncycling MCF-7/ADR cells was confirmed by the appearance of an apoptotic sub-$G_0/G_1$ peak and by the activation of caspase-3 (FIG. 3(b), left panel). MCF-7 wild type cells were growth-arrested but did not show any apoptotic features. Surprisingly, normal peripheral blood lymphocytes exposed to as much as 1000-fold higher concentrations of TB compound IK-178 for 72 hours had no loss of viability.

These results demonstrated that stationary MCF-7/ADR cells (with MDR), but not wild type MCF-7 cells (without MDR), die following treatment with indanocine. The ability of the TB compounds of the invention to induce apoptosis in stationary phase MDR cells was then studied in cells with collateral sensitivity to the TB compounds of the invention (HL-60/ADR (with MDR) and, for comparison, HL-60 (without MDR) cells).

First, the stage at which the TB compounds of the invention arrest growth of HL-60 and HL-60/ADR cells was determined by FACS analysis and caspase-3 activation as described above. As shown in FIG. 4, non-cycling HL-60/ADR cells became apoptotic when treated with TB IK-178.

Figure 5:
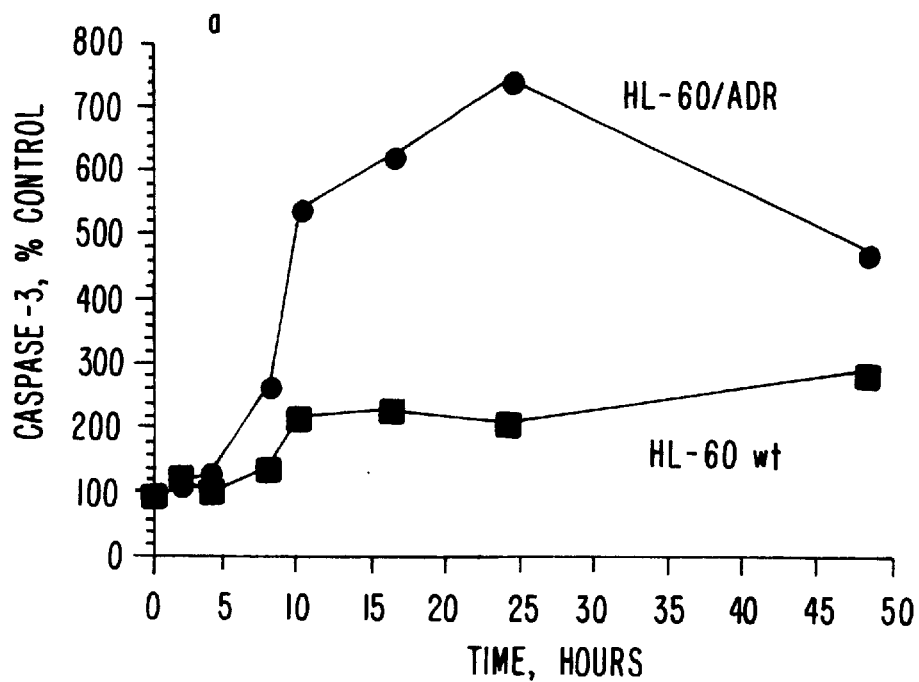
FIG. 5(a) displays results evidencing the occurrence of apoptosis in MDR and wt cells (HL-60 and HL-60/ADR) treated with the TB compounds of the invention (as represented by IK-178). Apoptosis was measured as a function of caspase-3 activity using the specific fluorigenic substrate DEVD-AMC. Caspace activity is represented along the y axis of each graph, while the time in hours following treatment with IK-178 (10 nM) is shown along the x axis.
FIG. 5(b) compares the effects of IK-78 and colchicine on caspase-3 activity.
Figure 5:
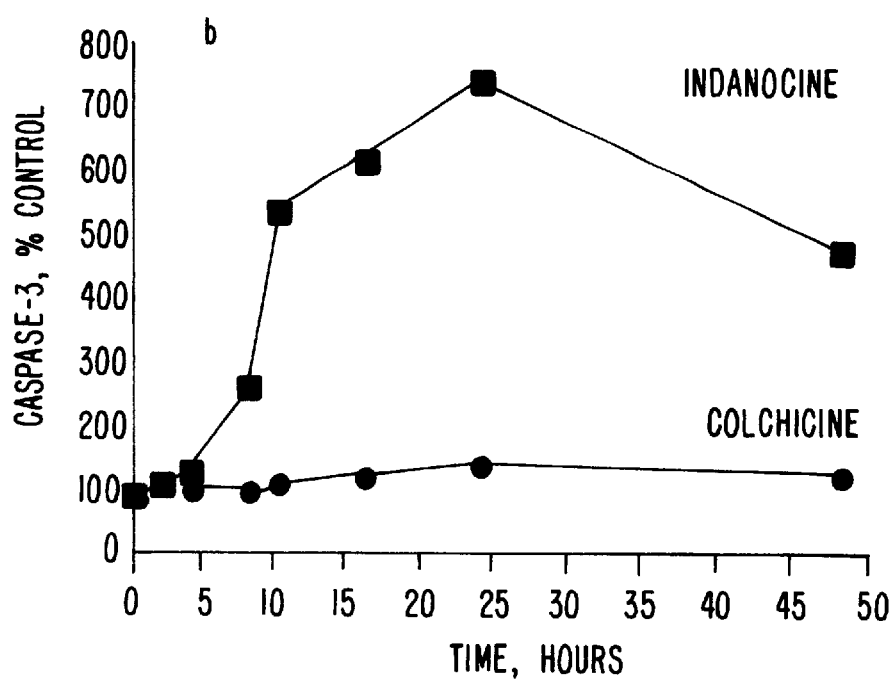

In the experiment whose results are shown in FIG. 5, TB compound IK-178 was tested for the ability to induce activation of the "executioner" caspase-3 in parental and multidrug resistant HL-60 cells. Caspase activity was measured using the fluorigenic caspase-3 specific substrate DEVD-AMC.

Briefly, cell extracts were prepared from 5×10$^6$ cells in 100 µl of a lysis buffer (25 mM TrisHCl, pH 7.5, 150 mM KCl, 5 mM EDNA, 1% Nonidet P-40, 0.5% sodium deoxycholate, and 0.1% SDS) and maintained on ice for 10 min, followed by centrifugation at 14,000×g for 5 min at 4° C. The resulting supernatants were collected and frozen at −80° C. or used immediately. Lysates (20 µl, 5–10 µg of total protein) were mixed with 30 µl of assay buffer (50 mM PIPES, 50 mM KC, 5 mM EGTA, 2 mM MgCl$_2$, 10 mM dithiothreitol (DTT), and 0.1 phenylmethanesulfonyl fluoride (PMSF)), containing 100 µM of Z-DEVD-AFC. Caspase-3-like protease activity was measured at 37° C. using a spectrofluorometric plate reader (Perkin-Elmer, LS50B) in the kinetic mode with excitation and emission wavelengths of 400 and 505 nm, respectively. Activity was measured by the release of 7-amino-4-methyl-coumarin (AMC) from the synthetic substrate Z-DEVD-AFC (Biomol, Plymouth Meeting, Pa.).

HL-60/ADR cells incubated with 10 nM of TB compound IK-178 showed a time-dependent increase in caspase-3 activity compared with untreated cells, reaching a maximum at 24 hours (FIG. 5(a), left panel). In contrast, HL-60 wild type cells showed only a slight increase I caspase-3 activity, about a quarter of the level obtained in the multidrug resistant cells (FIG. 5(a), left panel).

As a control, the effects of the antimitotic agent colchicine on caspase-3 activation in HL-60 cells was tested. Although colchicine and the TB compounds of the invention probably bind to the same site on tubulin (see below), colchicine did not activate caspase-3 (FIG. 5(b), right panel), and did not induce the apoptosis which TB compound IK-178 did induce in the HL-60/ADR cells.

Example VII

Effect of the TB Compounds of the Invention on Cellular Tubulin

Figure 6:
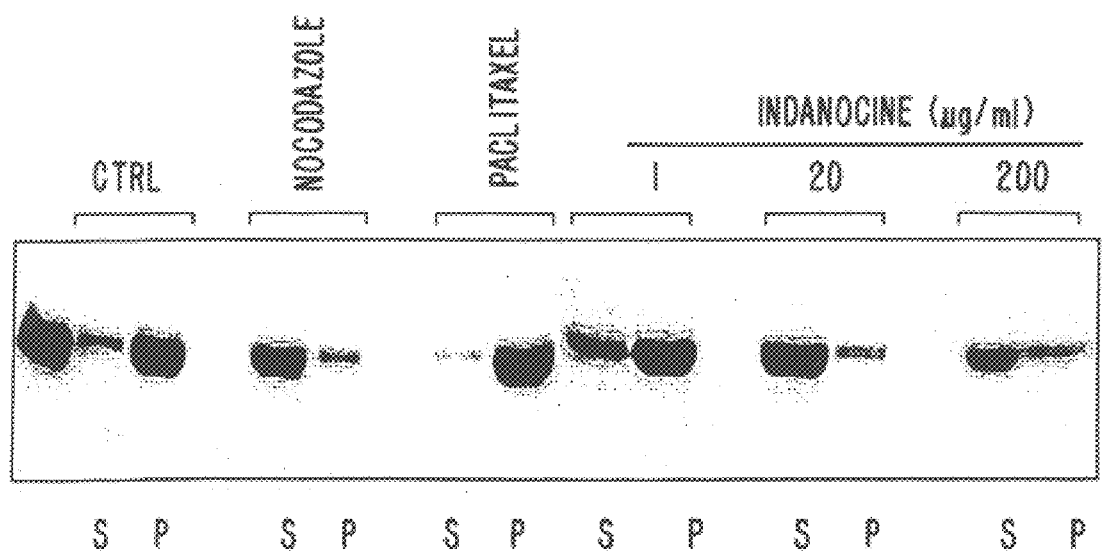
FIG. 6 displays results evidencing the effect of TB compound no. IK-178 on tubulin polymerization. Concentrations of IK-178 and, for comparison, of paclitaxel, are shown along the top of the drawing. "S" and "P" along the bottom of the drawing refer to treated supernatant and pellet, respectively. Darkly shaded bands represent polymerized tubulin.

TB drugs are those which interfere with cellular microtubules by interacting with tubulin to inhibit tubulin assembly or induce tubulin polymerization. As shown in FIG. 6, the compounds of the invention act as TB compounds in that they inhibit tubulin assembly, in a manner comparable to the known TB drug nocodazole, rather than induce tubulin polymerization.

To evaluate the effects of the TB compounds of the invention on tubulin, bovine brain tubulin (2.2 mg/ml) was incubated in PEM80 (80 mM K-PIPES, 1 mM MgCl$_2$, 1 mM EGTA) containing 10% glycerol and 2 mM GTP for 30 minutes at 37° C. in the presence or absence of 20 µg/ml nocodazole, 1 mM paclitaxel, or TB compound no. IK-178 at various concentrations. Tubulin polymer was resolved from monomer by sedimentation through a cushion of 60% glycerol in PEM80 at 70,000 rpm for 30 min at 37° C. in a Beckman TLA100 rotor. A fraction of the supernatant was removed for analysis, the cushion washed and then aspirated, and the pellet resuspended in SDS-PAGE sample buffer. Equal proportions of the supernatant and the pellet were then resolved by SDS-PAGE and tubulin visualized by staining with Coomassie blue.

The quantitative assessment of drug inhibition of tubulin polymerization and evaluation of inhibition of [$^3$H] colchicine binding to tubulin were then performed. In brief, for inhibition of assembly, 10 µM (1.0 mg/ml) tubulin was preincubated with varying drug concentrations (4% v/v dimethylsulfoxide as drug solvent) in 0.8 M monosodium glutamate for 15 min at 30° C. Samples were placed on ice and GTP (0.4 mM) was added. Reaction mixtures were transferred to 0° C. cuvettes in Gilford 250 spectrophotometers, baselines were establishes/d, and the temperature was jumped to 30° C. with electronic temperature controllers (about 60 sec). The IC$^{50}$ was defined as the drug concentration required to inhibit extent of assembly after a 20 min incubation. For the colchicine binding assay, reaction mixtures contained 1.0 µM (0.1 mg/ml) tubulin and 5.0 µM [$^3$H] colchicine and were incubated for 10 min at 37° C. prior to filtration through a stack of two DEAE-cellulose filters. At this time point, in reaction mixtures without inhibitor, binding is 40–50% of maximum in order to obtain data pertinent to inhibition of the rate of binding of colchicine to tubulin.

The TB compounds of the invention (as represented by TB compound IK-178), are nearly as potent as the strong tubulin assembly inhibitor, combretastatin A-4 (CS-A4). In particular, the GI$^{50}$ inhibitory concentration of CS-A4 was 1.2±0.03 µM (n=4), while that of TB compound IK-178 was 1.7±0.1 µM (n=3). Both compounds practically eliminated the binding of 5 µM [$^3$H]colchicine to 1 µM tubulin when present at 5 µM, with 98=/−4% inhibition (n=4) with CS-A4 and 95±2% (n=4) inhibition with indanocine. Neither agent inhibited the binding of [$^3$H]vinblastine to tubulin (single experiment).

The instant invention is shown and described herein in what are currently considered to be the most practical and preferred embodiments. It is recognized however, that departures may be made therefrom which are within the scope of the invention and that obvious modifications will occur to one skilled in the art upon reading this disclosure.

What is claimed is:

1. A compound having the structural formula:

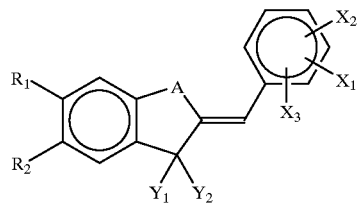

wherein,

A is (CH$_2$)$_n$, and n is 1 or 2;

R$_1$ and R$_2$ are each independently OR, lower alkoxy, halo, NO, NO$_2$, NH$_2$, acyl, acyloxy, acylamino, diacyl, carboxyacyl, amino-oxalyl, or together form —O—(CH$_2$)$_a$—O—, where a is 1, 2, or 3; and R$_1$ may also be alkyl; but R$_1$ and R$_2$ cannot both be OH; and, where X$_1$, X$_2$ or X$_3$ is lower alkoxy, R$_1$ and R$_2$ cannot both be methyloxy;

Y$_1$ and Y$_2$ are each independently H, OH, NH$_2$, carboxyl or together form =O or =NOH;

X$_2$ and X$_3$ are each independently halo, lower alkyl, lower alkoxy, NO$_2$, acyl, acyloxy, aryl, heteroaryl, acylphosphonate, or together form —O—(CH$_2$)$_b$—O—, where b is 1, 2, or 3; and, X$_1$ is H, OH, lower alkyl, lower alkoxy, NH$_2$, acyl, acyloxy, aryl, heteroaryl, acylphosphonate, or X$_1$ may form —O—(CH$_2$)$_b$—O— together with either X$_2$ or X$_3$, where b is 1, 2, or 3.

2. The compound of claim 1, wherein n is 1.

3. The compound of claim 2, wherein Y$_1$ and Y$_2$ together form =O.

4. The compound of claim 2, wherein R$_1$ and R$_2$ are each CH$_3$O.

5. The compound of claim 4, wherein X$_2$ is 3-OCH$_3$ and X$_3$ is 5-OCH$_3$.

6. The compound of claim 3, wherein X$_2$ is 3-CH$_3$ and X$_3$ is 5-CH$_3$.

7. The compound of claim 3, wherein X$_2$ and X$_3$ are halo.

8. The compound of claim 7, wherein X$_2$ and X$_3$ are iodo, and X$_1$ is OH.

9. The compound of claim 7, wherein X$_2$ and X$_3$ are chloro.

10. The compound of claim 9, wherein X$_1$ is pyridin-4-yl.

11. The compound of claim 3, wherein X$_2$ and X$_3$ are CH$_3$.

12. The compound of claim 11, wherein X$_1$ is 4-phosphonoacetyl.

13. The compound of claim 2, wherein X$_2$ and X$_3$ are NO$_2$.

14. The compound of claim 2, wherein Y$_1$ is H and Y$_2$ is OH, NH, or carboxyl.

15. The compound of claim 14, wherein X$_1$ and X$_2$ are CH$_3$.

16. The compound of claim 1, wherein X$_1$ and X$_2$ are CH$_3$, and Y1 and Y$_2$ together form =O.

17. A compound having the structural formula:

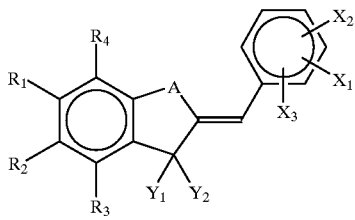

wherein,
A is $(CH_2)n$, and n is 1 or 2;
$R_1$ and $R_2$ are each independently, OH, lower alkoxy, halo, NO, $NO_2$, $NH_2$, acyl, acyloxy, acylamino, diacyl, carboxyacyl, amino-oxalyl, or together form —O—$(CH_2)_a$—O—, where a is 1, 2, or 3; ; and $R_1$ may also be alkyl except that $R_1$ and $R_2$ cannot both be OH or methyloxy;
$R_3$ is H, $NO_2$, $NH_2$, acyloxy, carboxyacyl, or O—C—O—Z, where Z is O-aryl or —CO-carboxyacyl;
$R_4$ is H, acyl, acyloxy or carboxyacyl;
$Y_1$ and $Y_2$ are each independently H, OH, $NH_2$, carboxyl or together form =O or =NOH;
$X_2$ and $X_3$ are each halo, lower alkyl, lower alkoxy, $NO_2$, $NH_2$, acyl, acyloxy, aryl, heteroaryl, acylphosphonate, or together form —O—$(CH_2)_b$—O—, where b is 1, 2, or 3; and,
$X_1$ is H, OH, lower alkyl, lower alkoxy, $NO_2$, $NH_2$, acyl, acyloxy, aryl, heteroaryl, acylphosphonate, or $X_1$ may form —O—$(CH_2)_b$—O— together with either $X_2$ or $X_3$, where b is 1, 2, or 3.

18. The compound of claim 17, wherein A is $CH_2$; $R_1$ is methyl; $Y_1$ and $Y_2$ together form =O or =NOH; $X_2$ and $X_3$ are methyl or methyloxy; and $X_1$ is H, OH, or $NH_2$.

19. The compound of claim 17, wherein $R_1$ is methyl; $R_3$ is H; $Y_1$ and $Y_2$ together form =O; $X_2$ and $X_3$ are each methyl; and $X_1$ is H.

20. The compound of claim 17, wherein $R_1$ is methyl; $R_3$ is H; $Y_1$ and $Y_2$ together form =O; $X_2$ and $X_3$ are methyl; and $X_1$ is OH.

21. The compound of claim 18, wherein $R_3$ is $NH_2$.

22. The compound of claim 21, wherein $X_1$ is $NH_2$.

23. A pharmaceutical composition comprising the compound of claim 1 and a pharmaceutically acceptable carrier.

24. A pharmaceutical composition comprising the compound of claim 17 and a pharmaceutically acceptable carrier.

25. A pharmaceutical composition comprising the compound of any of claims 18, 19, 20, 21 or 22, together with a pharmaceutically acceptable carrier.

26. A method for inhibiting the growth of malignant cells in a host, comprising administering the compound of claim 1 to the host in a manner which will bring the compound into contact with the malignant cells.

27. A method for inhibiting the growth of malignant, multiple drug resistant (MDR) cells in a host, comprising administering the compound of claim 1 to the host in a manner which will bring the compound into contact with the malignant, MDR cells.

28. A method for inhibiting the growth of stationary phase malignant, multiple drug resistant (MDR) cells in a host, comprising administering the compound of claim 1 to the host in a manner which will bring the compound into contact with the stationary phase malignant, MDR cells.

29. A method for inhibiting the growth of malignant cells in a host, comprising administering the compound of claim 17 to the host in a manner which will bring the compound into contact with the malignant cells.

30. A method for inhibiting the growth of malignant, multiple drug resistant (MDR) cells in a host, comprising administering the compound of claim 17 to the host in a manner which will bring the compound into contact with the malignant, MDR cells.

31. A method for inhibiting the growth of stationary phase malignant, multiple drug resistant (MDR) cells in a host, comprising administering the compound of claim 17 to the host in a manner which will bring the compound into contact with the stationary phase malignant, MDR cells.

32. A method for inhibiting the growth of malignant cells in a host, comprising administering the compound of any of claims 18, 19, 20, 21 or 22 to the host in a manner which will bring the compound into contact with the malignant cells.

33. A method for inhibiting the growth of malignant, multiple drug resistant (MDR) cells in a host, comprising administering the compound of any of claims 18, 19, 20, 21 or 22 to the host in a manner which will bring the compound into contact with the malignant, MDR cells.

34. A method for inhibiting the growth of stationary phase malignant, multiple drug resistant (MDR) cells in a host, comprising administering the compound of any of claims 18, 19, 20, 21 or 22 to the host in a manner which will bring the compound into contact with the stationary phase malignant, MDR cells.

35. A method for inhibiting the growth of virus-infected cells in a host, comprising administering the compound of claim 1 to the host in a manner which will bring the compound into contact with the virus-infected cells.

36. A method for inhibiting the growth of virus-infected, multiple drug resistant (MDR) cells in a host, comprising administering the compound of claim 1 to the host in a manner which will bring the compound into contact with the virus-infected, MDR cells.

37. A method for inhibiting the growth of virus-infected cells in a host, comprising administering the compound of claim 17 to the host in a manner which will bring the compound into contact with the virus-infected cells.

38. A method for inhibiting the growth of virus-infected, multiple drug resistant (MDR) cells in a host, comprising administering the compound of claim 17 to the host in a manner which will bring the compound into contact with the virus-infected, MDR cells.

39. A method for inhibiting the growth of virus-infected cells in a host, comprising administering the compound of any of claims 18, 19, 20, 21 or 22 to the host in a manner which will bring the compound into contact with the virus-infected cells.

40. A method for inhibiting The growth of virus-infected, multiple drug resistant (MDR) cells in a host, comprising administering the compound of any of claims 18, 19, 20, 21 or 22 to the host in a manner which will bring the compound into contact with the virus-infected, MDR cells.

41. The compound of claim 1, wherein $X_1$ is acylphosphonate.

42. The compound of claim 17, wherein $X_1$ is acylphosphonate.

* * * * *

UNITED STATES PATENT AND TRADEMARK OFFICE
CERTIFICATE OF CORRECTION

PATENT NO.   : 6,162,810
DATED        : December 19, 2000
INVENTOR(S)  : Dennis A. Carson et al.

It is certified that error appears in the above-identified patent and that said Letters Patent is hereby corrected as shown below:

Title page,
Item [54], Title, change "INADONE" to -- INDANONE --.
Item [57], ABSTRACT,
Line 1, change "inadone" to -- indanone --.

Column 22,
Line 18, change "OR" to -- OH --.

Column 23,
Line 19, after "except that", insert -- where $X_1$, $X_2$ or $X_3$ is lower alkoxy, --.

Signed and Sealed this

Eighteenth Day of October, 2005

JON W. DUDAS
*Director of the United States Patent and Trademark Office*